United States Patent [19]

Chokai et al.

[11] Patent Number: 5,432,195

[45] Date of Patent: Jul. 11, 1995

[54] BENZOFURAN DERIVATIVE AND PHARMACEUTICAL COMPOSITION

[75] Inventors: Shoichi Chokai, Kyoto; Shinji Ohmachi; Masafumi Taira, both of Shiga, all of Japan

[73] Assignee: Nippon Shinyaku Company Limited, Japan

[21] Appl. No.: 175,383

[22] PCT Filed: Jul. 8, 1992

[86] PCT No.: PCT/JP92/00875

§ 371 Date: Jan. 5, 1994

§ 102(e) Date: Jan. 5, 1994

[87] PCT Pub. No.: WO93/01180

PCT Pub. Date: Jan. 21, 1993

[30] Foreign Application Priority Data

Jul. 9, 1991 [JP] Japan .................................. 3-195722
Apr. 10, 1992 [JP] Japan .................................. 4-118076
May 8, 1992 [JP] Japan .................................. 4-143423

[51] Int. Cl.$^6$ .................. A61K 31/34; C07D 307/78; C07D 307/85
[52] U.S. Cl. .................................. 514/469; 549/462; 549/468; 549/471
[58] Field of Search ............ 549/462, 468, 471; 514/469

[56] References Cited

U.S. PATENT DOCUMENTS 4,918,092  4/1990  Frenette .............................. 514/382

OTHER PUBLICATIONS

Hackh's "Chemical Dictionary" McGraw-Hill, 1983, p. 16.
Clarkson et al. "The Role of individual Differences in Lipoprotein . . . of atherosclerosis" N.Y. Aca. Sci. vol. 454, pp. 28–43 (1985).
Eaton. "High density lipoprotein" J. Chron. Dis. 31 131–135 (1978).
Pike et al. "Nutrition au integrated approach" John Wiley & Sons. p. 534 (1984).
Journal of the Chemical Society, Perkin Transactions 1, No. 9, 1978, Letchworth GB, pp. 928–933, S. Jordan et al.–The synthesis and oxidation . . . Toliprolol.

Primary Examiner—Ceila Chang
Attorney, Agent, or Firm—Rosenman & Colin

[57] ABSTRACT

The present invention relates to a compound expressed by the following general formula (I), pharmacologically-acceptable salt thereof and pharmaceutical composition mainly comprising the same.

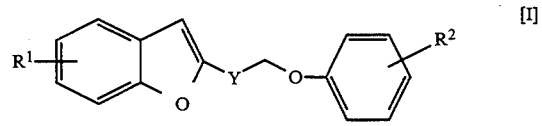

wherein $R^1$ is hydrogen, halogen or alkyl; $R^2$ is alkoxycarbonyl, aralkyloxycarbonyl, carboxy, hydroxyalkyl or acyloxyalkyl; Y is >CHOH, >CHOZ, >CH$_2$ or >CO; and Z is acyl.

The pharmaceutical composition of the present invention is effective for prevention and therapy of arteriosclerosis, ischemic heart diseases, cerebral infarction and restenosis after PTCA operations.

42 Claims, No Drawings

BENZOFURAN DERIVATIVE AND PHARMACEUTICAL COMPOSITION

This application is a 371 of PCT/JP92/00875 filed Jul. 8, 1992.

TECHNICAL FIELD

The present invention relates to a novel benzofuran derivative, expressed by the following general formula (I) and pharmacologically-acceptable salt thereof, which exhibits a therapeutic action for diseases caused by high Lp(a) concentration in blood and a lowering action for lipid concentration in blood and are useful for therapy and prevention of coronary diseases, cerebral infarction, hyperlipemia and arteriosclerosis.

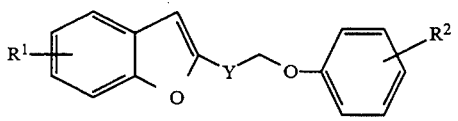

wherein $R^1$ is hydrogen, halogen or alkyl; $R^2$ is alkoxycarbonyl, aralkyloxycarbonyl, carboxy, hydroxyalkyl or acyloxyalkyl; Y is >CHOH, >CHOZ, >CH$_2$ or >CO; and z is acyl.

BACKGROUND ART

Lp(a) was firstly found in blood of patients suffering from arteriosclerosis and has been considered to be a fatal factor for arteriosclerosis. Today, it has been known as a kind of lipoprotein having apoprotein B-100 (the same as LDL molecule) at the central part to which apoprotein (a) is bonded. (cf. Gendai Iryou, vol.22, no.7, 1990).

Lp(a) is detected only in Primates including human being. Therefore, it is difficult to subject to animal experiment using rodents and the like whereby its investigation of its behavior in animals has been delayed.

Lp(a) has the same fundamental structure as plasminogen and, accordingly, Lp(a) is supposed to participate in inhibition of decomposition of fibrin in blood resulting in inhibition of dissolution of thrombosis.

Lp(a) is distributed in the area where arteriosclerosis may take place in higher concentrations than other areas whereby Lp(a) is presumed to directly participate in arteriosclerosis. In addition, the concentration of Lp(a) in blood is not affected by conventional hypolipemic drugs and arteriosclerosis is observed even in the people with low lipid level. Consequently, the relation between Lp(a) and arteriosclerosis has been considered to be important.

It has been known that the Lp(a) of the patients of arteriosclerosis and hyperlipemia never lowers in blood by a diet therapy.

It has been known that high Lp(a) concentration in blood is dominated and decided by genetic factor.

Out of the above-given knowledges, it may be easily concluded that Lp(a) is directly related to arteriosclerosis and is based upon the inhibitory action of dissolution of thrombosis.

DISCLOSURE OF INVENTION

Since it has been found to be quite likely that Lp(a) is a lipoprotein which accelerates the arteriosclerosis, there has been attempts to prevent those disease by curing the diseases with high Lp(a) concentration in blood (cf. Arteriosclerosis, vol.10, no.5, pages 672–679, 1990). Nicotinic acid has been known as a substance which lowers the concentration of Lp(a) in blood though it exhibits adverse reactions such as flushing and, moreover, the main action is not so satisfactory (J. Internal Medicine 226 271–276 (1989)).

Incidentally, it has been widely known that, besides the lowering action of Lp(a) concentration, the substances which lower the lipid concentration in blood are useful for the therapy of arteriosclerosis. Accordingly, it is presumed that, if there is a substance which lowers the Lp(a) concentration and also lowers the lipid level in blood, such a substance would be far useful for the therapy of the above-given diseases.

As a result thereof, the present inventors have found that the compound expressed by the general formula (I) met with the requirement and have achieved the present invention.

The characteristic feature of the present invention is the structure per se of the compounds expressed by the general formula (I). The compounds of the present invention are novel which have not been described in any of the prior art literatures yet.

Examples of the halogen expressed by $R^1$ in the general formula (I) are fluorine, chlorine, bromine and iodine.

Preferred examples of the alkyl are straight chain or branched having 1 to 7 carbon atoms and are, for example, methyl, ethyl, n-propyl, iso-propyl, n-butyl, iso-butyl, tert-butyl, n-pentyl, iso-pentyl, n-hexyl, iso-hexyl, n-heptyl and iso-heptyl.

Examples of the alkyl moiety in the alkoxycarbonyl expressed by $R^2$ are those which are exemplified as the alkyl for $R^1$ given hereinabove.

Preferred aralkyloxycarbonyl expressed by $R^2$ are those having 8 to 14 carbon atoms and the examples are benzyloxycarbonyl, 2-methylbenzyloxycarbonyl, 3-methylbenzyloxycarbonyl, 4-methylbenzyloxycarbonyl, phenethyloxycarbonyl, 3-phenylpropoxycarbonyl, 1-naphthylmethoxycarbonyl, 2-naphthylmethoxycarbonyl, 2-(1-naphthyl)ethoxycarbonyl and 3-(1-naphthyl)propoxycarbonyl.

Preferred examples of the hydroxyalkyl are straight chain or branched having 1 to 7 carbon atom(s) and are, for example, hydroxymethyl, 2-hydroxyethyl, 1-hydroxyethyl, 3-hydroxypropyl, 1-hydroxypropyl, 4-hydroxybutyl, 1-hydroxybutyl, 5-hydroxypentyl, 1-hydroxypentyl, 6-hydroxyhexyl, 1-hydroxyhexyl, 7-hydroxyheptyl and 1-hydroxyheptyl.

Preferred acyloxyalkyl is O-acyl derivative of the above hydroxyalkyl wherein preferred acyl is that with 1 to 11 carbon atom(s). Thus, the examples are formyl, acetyl, propionyl, butyryl, isobutyryl, valeryl, isovaleryl, sec-valeryl, benzoyl, 2-methylbenzoyl, 3-methylbenzoyl, 4-methylbenzoyl, 1-naphtoyl and 2-naphtoyl.

Preferred acyl expressed by Z is that with 1 to 11 carbon atom(s). The examples are formyl, acetyl, propionyl, butyryl, isobutyryl, valeryl, isovaleryl, sec-valeryl, benzoyl, 2-methylbenzoyl, 3-methylbenzoyl, 4-methylbenzoyl, 1-naphtoyl and 2-naphtoyl.

When $R^2$ is carboxy, the compounds of the present invention may be used in a free form or in a form of a pharmacologically-acceptable salt prepared by conventional means. Examples of the salt are alkali metal salts such as sodium salts and alkali earth metal salts such as calcium salts.

In addition to the compounds which will be given in the Examples hereinafter, the compounds of the present invention further include the following compounds which, however, are intended to exemplify only a part of the present invention compounds and are not intended to limit the scope of the present invention thereto.

5-tert-Butyl-2-[2-(3-carboxyphenoxy)-1-hydroxyethyl]benzofuran;
5-tert-Butyl-2-[2-(2-carboxyphenoxy)-1-hydroxyethyl]benzofuran;
5-tert-Butyl-2-[1-hydroxy-2-(4-hydroxymethylphenoxy)ethyl]benzofuran;
5-tert-Butyl-2-[1-hydroxy-2-(3-hydroxymethylphenoxy)ethyl]benzofuran;
2-[2-(4-Ethoxycarbonylphenoxy)-1-hydroxyethyl]-5-fluorobenzofuran;
5-Chloro-2-[1-hydroxy-2-(3-propyloxycarbonylphenoxy)ethyl]benzofuran;
5-Bromo-2-[1-hydroxy-2-(4-isopropyloxycarbonylphenoxy)ethyl]benzofuran;
2-[2-(3-Butoxycarbonylphenoxy)-1-hydroxyethyl]-5-iodobenzofuran;
2-[2-(3-tert-Butoxycarbonylphenoxy)-1-hydroxyethyl]-5-methylbenzofuran;
6-Ethyl-2-[1-hydroxy-2-(2-pentyloxycarbonylphenoxy)ethyl]benzofuran;
2-[2-(4-Hexyloxycarbonylphenoxy)-1-hydroxyethyl]-5-propylbenzofuran;
2-[2-(3-Heptyloxycarbonylphenoxy)-1-hydroxyethyl]-5-isopropylbenzofuran;
5-Butyl-2-[1-hydroxy-2-(4-hydroxymethylphenoxy)ethyl]benzofuran;
2-[1-Hydroxy-2-[2-(1-hydroxyethyl)phenoxy]ethyl]-6-pentylbenzofuran;
5-Hexyl-2-[1-hydroxy-2-[4-(3-hydroxypropyl)phenoxy]ethyl]benzofuran;
6-Heptyl-2-[1-hydroxy-2-[4-(1-hydroxypropyl)phenoxy]ethyl]benzofuran;
2-[1-Hydroxy-2-[2-(4-hydroxybutyl)phenoxy]ethyl]benzofuran;
6-Fluoro-2-[1-hydroxy-2-[4-(1-hydroxybutyl)phenoxy]ethyl]benzofuran;
2-[1-Hydroxy-2-[4-(2-hydroxyethyl)phenoxy]ethyl]-6-methylbenzofuran;
5-Chloro-2-[1-hydroxy-2-[4-(1-hydroxypentyl)phenoxy]ethyl]benzofuran;
5-Bromo-2-[1-hydroxy-2-[3-(1-hydroxyhexyl)phenoxy]ethyl]benzofuran;
2-[1-Hydroxy-2-[2-(6-hydroxyhexyl)phenoxy]ethyl]-5-propylbenzofuran;
5-Isopropyl-2-[1-hydroxy-2-[4-(7-hydroxyheptyl)phenoxy]ethyl]benzofuran;
6-tert-Butyl-2-[1-hydroxy-2-[4-(1-hydroxyheptyl)phenoxy]ethyl]benzofuran;
2-[1-Acetoxy-2-(4-methoxycarbonylphenoxy)ethyl]-5-tert-butylbenzofuran;
2-[1-Acetoxy-2-(4-carboxyphenoxy)ethyl]-5-tert-butylbenzofuran;
2-[1-Benzoyloxy-2-(4-methoxycarbonylphenoxy)ethyl]-5-tert-butylbenzofuran;
2-[1-Benzoyloxy-2-(4-carboxyphenoxy)ethyl]-5-tert-butylbenzofuran;
5-tert-Butyl-2-[2-(4-methoxycarbonylphenoxy)-1-propionyloxyethyl]benzofuran;
5-tert-Butyl-2-[2-(4-carboxyphenoxy)-1-propionyloxyethyl]benzofuran;
5-tert-Butyl-2-[1-butyryloxy-2-(4-methoxycarbonylphenoxy)ethyl]benzofuran;
5-tert-Butyl-2-[1-butyryloxy-2-(4-carboxyphenoxy)ethyl]benzofuran;
5-tert-Butyl-2-[2-(4-methoxycarbonylphenoxy)-1-(1-naphthoyloxy)ethyl]benzofuran;
5-tert-Butyl-2-[2-(4-carboxyphenoxy)-1-(1-naphthoyloxy)ethyl]benzofuran;
5-tert-Butyl-2-[2-(4-methoxycarbonylphenoxy)-1-(2-naphthoyloxy)ethyl]benzofuran;
5-tert-Butyl-2-[2-(4-carboxyphenoxy)-1-(2-naphthoyloxy)ethyl]benzofuran;
5-tert-Butyl-2-(4-hydroxymethylphenoxyacetyl)benzofuran;
2-(4-Acetoxymethylphenoxyacetyl)-5-tert-butylbenzofuran;
2-[1-Acetoxy-2-(4-acetoxymethylphenoxy)ethyl]-5-tert-butylbenzofuran;
5-tert-Butyl-2-[2-(4-carboxyphenoxy)ethyl]benzofuran;
5-tert-Butyl-2-[2-(4-methoxycarbonylphenoxy)ethyl]benzofuran;
2-[2-(4-hydroxymethylphenoxy)ethyl]-5-isopropylbenzofuran; and
2-[2-(4-Acetoxymethylphenoxy)ethyl]-5-chlorobenzofuran.

All of the compounds in accordance with the present invention are novel and have not been described in any of the prior art literature yet. They may, for example, be manufactured by the method as given below.

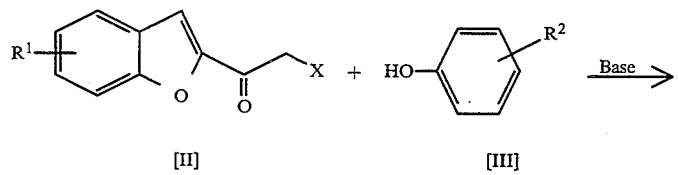

[II]  [III]

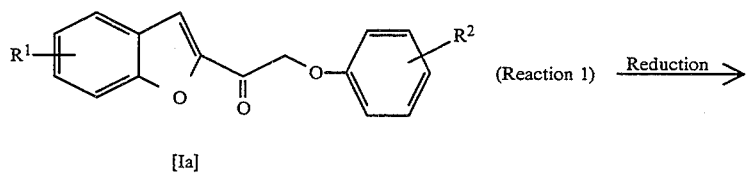

(Reaction 1)

[Ia]

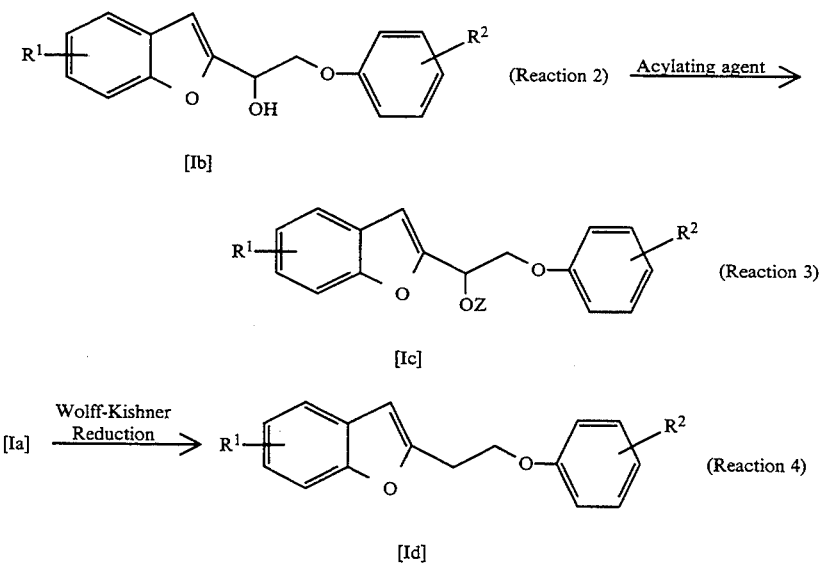

wherein $R^1$, $R^2$ and Z are the same as those defined already and X is halogen, alkylsulfonyloxy or arylsulfonyloxy.

Thus, the compound (II) is made to react with the compound (III) in the presence of a base to give a compound (Ia) (Reaction 1). The compound (Ia) is reduced to give a compound (Ib) (Reaction 2). The compound (Ib) is O-acylated to give a compound (Ic) (Reaction 3). The compound (Ia) is subjected to Wolff-Kishner reduction to give a compound (Id) (Reaction 4).

(Reaction 1)

The reaction of the compound (II) with the compound (III) can be usually conducted in aprotic solvent (e.g. polar solvents such as acetonitrile and N,N-dimethylformamide; ethers such as tetrahydrofuran and diethyl ether; halogenated hydrocarbons such as chloroform and methylene chloride; and hydrocarbons such as benzene, toluene and n-hexane) in the presence of a base (e.g. potassium carbonate, sodium carbonate, pyridine and triethylamine) at the temperature of from $-20°$ to $100°$ C.

The reaction time may vary depending upon the type of the compounds (II) and (III) and also upon the reaction temperature but, usually, 30 minutes to 24 hours will be suitable. Preferred amount of the compound (III) to 1 mol of the compound (II) is from 1 to 1.2 mol.

(Reaction 2)

When the compound (Ia) used as a starting material and the method of reduction are different, then the compound (Ib) with different structure is obtained. As hereunder, the Reaction 2 will be illustrated in the order of the structure of $R^2$ in the compound (Ib).

1) When $R^2$ is alkoxycarbonyl, aralkyloxycarbonyl or acyloxyalkyl:

In case that ester ($R^2$=alkoxycarbonyl, aralkyloxycarbonyl or acyloxyalkyl) is used as the compound (Ia), metal hydride complex (e.g. sodiumborohydride or sodium cyanoborohydride), diborane or the like can be used as a reducing agent to give a compound (Ib), while, in case that the same compound (Ia) (excluding the case where $R^2$ is benzyloxycarbonyl) as above is used, a catalytic hydrogenation can be used.

When metal hydride complex or diborane or the like is used, the reaction can be conducted at the temperature of $-20°$ to $100°$ C. in a suitable solvent. Preffered example of the solvent is such as polar solvent (e.g. water, methanol, ethanol, isopropanol, N,N-dimethylformamide or dimethyl sulfoxide) provided that sodium borohydride or sodium cyanoborohydride is used while, in case diborane is used, preffered solvent is an ether type solvent (e.g. tetrahydrofuran, diethyl ether or diethylene glycol dimethyl ether).

The reaction time may vary depending upon the type of the compound (Ia) and the reducing agent and also upon the reaction temperature but, usually, 30 minutes to 24 hours will be suitable.

The amount of the reducing agent may vary depending upon the type of the reducing agent but, preferably, it is 0.5–2.4 mol to one mol of the compound (Ia).

When catalytic hydrogenation is adopted, the hydrogenation can be carried out at ambient temperature and ordinary pressure in a suitable solvent (such as alcoholic solvent [e.g. methanol, ethanol, etc.]; aqueous alcoholic solvent; or ether type solvent [e.g. dioxane or tetrahydrofuran]) in the presence of a catalysts such as palladium carbon, platinum oxide, ruthenium carbon and Raney nickel. Depending upon the type of the compound (Ia) or the catalyst used, the reaction may be conducted with cooling or heating or under pressure.

The reaction time may vary depending upon the type of the compound (Ia) or the catalyst but, usually, it will be from 30 minutes to 24 hours.

The amount of the catalyst may vary depending upon the type of the catalyst though, preferably, it is 1–20% to the amount of the compound (Ia).

2) When $R^2$ is carboxy:

When carboxylic acid ($R^2$ is carboxy) is used as the compound (Ia), metal hydride complex (e.g. sodium borohydride or sodium cyanoborohydride) is used as a reducing agent and the reaction can be carried out by the same manner as in the case of the above 1) wherein the metal hydride complex is used, or catalytic hydrogenation can be carried out by the same manner as in the case of the above 1) wherein catalytic hydrogenation is carried out.

When benzyl ester ($R^2$ is benzyloxycarbonyl) is used as the compound (Ia), the reaction can be the same as in the case of the above 1) wherein catalytic hydrogenation is carried out.

3) When $R^2$ is hydroxyalkyl:

In case that hydroxyalkyl compound ($R^2$ is hydroxyalkyl) is used as the compound (Ia), metal hydride complex (e.g. sodiumborohydride, sodium cyanoborohydride, lithium aluminum hydride or lithium trimethoxyaluminum hydride), diborane or the like can be used as a reducing agent to give a compound (Ib), while, in case that the same compound (Ia) (excluding the case where $R^2$ is hydroxymethyl) as above is used, a catalytic hydrogenation can be used.

When ester ($R^2$ is alkoxycarbonyl, aralkyloxycarbonyl or acyloxyalkyl) is used as the compound (Ia), metal hydride complex (e.g. lithium aluminum hydride or lithium trimethoxyaluminum hydride) can be used as a reducing agent.

When carboxylic acid ($R^2$ is carboxy) is used as a compound (Ia), metal hydride complex (e.g. lithium aluminum hydride or lithium trimethoxyaluminum hydride), diborane or the like can be used as a reducing agent.

The compound (Ib) may also be manufactured starting from the oxoalkyl compound (Ia) ($R^2$ is oxoalkyl) (obtained by the reaction of the compound (II) with the compound (III) wherein $R^2$ is oxoalkyl) in accordance with the Reaction 1) by the same manner as in the case where the above hydroxyalkyl compound ($R^2$ is hydroxyalkyl) is used.

when metal hydride complex, diborane or the like is used, the reaction can be carried out at $-20°$ to $100°$ C. in a suitable solvent. Preffered solvent is ether type solvent such as tetrahydrofuran, diethyl ether or diethylene glycol dimethyl ether when lithium aluminum hydride or lithium trimethoxyaluminum hydride is used as a reducing agent while, when sodium borohydride, sodium cyanoborohydride or diborane is used, preffered solvent is the same as that used in the case of metal hydride complex or diborane in the above 1).

The reaction time may vary depending upon the types of the compound (Ia) and the reducing agent and also upon the reaction temperature but, usually, 30 minutes to 24 hours will be suitable.

The amount of the reducing agent may vary depending upon the type of the reducing agent used but, preferably, it is 0.5 to 2.4 mol to one mol of the compound (Ia).

(Reaction 3)

When the compound (Ib) is acylated using an acylating agent or the compound (Ib) is dehydrated/condensed using a suitable carboxylic acid and condensing agent, the compound (Ic) can be obtained.

when the acylating agent such as carboxylic acid anhydride (e.g. acetic anhydride, propionic anhydride and benzoic anhydride) or carboxylic acid halide (e.g. acetyl chloride, propionyl chloride or benzoyl chloride) is used, (Ib) can be made to react at $-20°$ to $100°$ C. in the presence of a base (e.g. potassium carbonate, sodium carbonate, pyridine or triethylamine) in the presence or absence of aprotic solvent such as polar solvent (e.g. acetonitrile or N,N-dimethylformamide), ether type solvent (e.g. tetrahydrofuran or diethyl ether), halogenated hydrocarbon (e.g. chloroform or methylene chloride) or hydrocarbon (e.g. benzene, toluene or n-hexane).

The reaction time may vary depending upon the type of the compound (Ib) or the acylating agent as well as the reaction temperature but, usually, it is 30 minutes to 24 hours. The preferred amount of the acylating agent to the compound (Ib) is 1 to 1.2 mol.

When the compound (Ib) wherein $R^2$ is hydroxyalkyl is used, the use of 2 or more mol of acylating agent to the compound (Ib) can give the compound (Ic) wherein $R^2$ is acyloxyalkyl.

When a condensing agent (e.g. N,N-dicyclohexylcarbodiimide, 2-chloro-N-methylpyridinium iodide or triphenylphosphine with carbon tetrachloride) is used, the compound (Ib) can be made to react with a suitable carboxylic acid (e.g. acetic acid, propionic acid or benzoic acid) in the above-given aprotic solvent at the temperature of $-20°$ to $100°$ C.

The reaction time may vary depending upon the type of the compound (Ib), carboxylic acid and condensing agent used as well as the reaction temperature but, usually, it is 30 minutes to 24 hours. Preferred amount of the carboxylic acid and the condensing agent to the compound (Ib) is 1 to 1.2 mol.

When the compound (Ib) wherein $R^2$ is hydroxyalkyl is used, the use of 2 or more mol of carboxylic acid and condensing agent to the compound (Ib) can give the compound (Ic) wherein $R^2$ is acyloxyalkyl.

The compound (Ia) may also be manufacured by oxidation of the compound (Ib) with the suitable oxidizing agent (e.g. permanganate, manganese dioxide, chromic acid, N-halocarboxylic amide, dimethylsulfoxide and the like).

(Reaction 4)

When the compound (Ia) wherein $R^2$ is carboxy or hydroxyalkyl is heated at $150°$–$250°$ C. with hydrazine monohydrate and base (e.g. sodium hydroxide or potassium hydroxide) in diethylene glycol, the compound (Id) wherein $R^2$ is carboxy or hydroxyalkyl is obtained.

When the compound (Ia) wherein $R^2$ is alkoxycarbonyl or aralkyloxycarbonyl is used, the reaction may be conducted in the same way as above to give the compound (Id) wherein $R^2$ is carboxy.

When the compound (Ia) wherein $R^2$ is acyloxyalkyl is used, the reaction may be conducted in the same way as above to give the compound (Id) wherein $R^2$ is hydroxyalkyl.

The compound (Id) wherein $R^2$ is alkoxycarbonyl or aralkyloxycarbonyl is obtained by esterizing the compound (Id) wherein $R^2$ is carboxy as hereinafter.

The compound (Id) wherein $R^2$ is acyloxyalkyl is obtained by reacting the compound (Id) wherein $R^2$ is hydroxyalkyl in the same manner as the Reaction 3.

When the compound (Ib) or the compound (Ic) is subjected to a catalytic hydrogenation, the compound (Id) (excluding the case wherein $R^2$ is hydroxymethyl or benzyloxycarbonyl) may also be manufacturerd.

The preferred solvent which may be used is alcoholic solvent (e.g. methanol, ethanol, propanol or isopropanol) or ether type solvent (e.g. tetrahydrofuran or dioxane). The reaction is carried out usually under ordinary pressure or pressure of 2–8 atm., and accelerated by adding acidic catalyst such as acetic acid or hydrochloric acid.

The compound (I) of the present invention wherein $R^2$ is carboxy may also be manufactured by hydrolysis of the ester ($R^2$ is alkoxycarbonyl or aralkyloxycarbonyl) prepared hereinabove.

Such hyrolysis reaction can be carried out in a solvent such as water, methanol, ethanol or a mixture thereof in the presence of a base such as potassium carbonate, sodium hydroxie or potassium hydroxide at the temperature of 0°–150° C. or, preferably, 20°–100° C.

The amount of the alkali to 1 mol of the ester (R² is alkoxycarbonyl or aralkyloxycarbonyl) is 1–5 mol or, preferably, 2–3 mol.

This hydrolysis reaction may also be conducted in the presence of mineral acid (e.g. hydrochloric acid, hydrobromic acid or sulfuric acid) in a suitable sovent (e.g. aqueous methanol, aqueous ethanol or other aqueous alcohol or acetic acid) at room temperature to 80° C.

The amount of the acid to 1 mol of the ester (R² is alkoxycarbonyl or aralkyloxycarbonyl) is 0.1–10 mol or, preferably, 0.2–3 mol.

The compound (I) of the present invention wherein R² is alkoxycarbonyl or aralkyloxycarbonyl may also be manufactured by esterification of the carboxylic acid (R² is carboxy) obtained hereinabove.

Said esterification reaction can be carried out by conventional means such as those by the use of diazomethane, alcohol in the presence of acid (e.g. hydrochloric acid, sulfuric acid, p-toluenesulfonic acid, etc.) or thionylchloride with alcohol.

When the compound (I) of the present invention prepared as such is a free carboxylic acid (R²=carboxy), said compound may be converted to salt by conventional means with pharmacologically-acceptable bases.

For example, alkali metal salt can be manufactured by hyrolysis of the ester (R² is alkoxycarbonyl or aralkyloxycarbonyl) manufactured hereinabove in alcohol or in aqueous alcohol using sodium hydroxide or potassium hydroxide in accordance with the above hydrolysis. Alternatively, the carboxylic acid (R² is carboxy) is treated with one equivalent amount of sodium hydroxide, potassium hydroxide, metal sodium, etc. preferably in alcoholic solvent whereupon the corresponding alkali metal salt can be prepared.

In the case of alkali earth metal salts, the alkali salt prepared as above is dissolved in water and an equivalent amount of calcium chloride or the like is added thereto whereupon the corresponding alkali earth metal salts can be prepared.

The desired compound (I) prepared as such or salt thereof can be isolated/purified from the reaction mixture by conventional isolating/purifying means such as, for example, extraction, concentration, neutralization, filtration, recrystallization, column chromatograhy, and thin layer chromatoaraphy.

Some of the compounds (I) of the present invention have two or more stereoisomers due to asymmetric carbon(s) and such isomers and a mixture thereof are also covered by the present invention.

Among the compound (I) of the present invention, optical compound due to asymmetric carbon substituted with hydroxyl group may be manufactured by an asymmetric reduction of compound (Ia) using a catalyst such as rhodium complex or ruthenium complex utilizing asymmetric ligand such as MCCPM, BINAP or BPPFOH. In such a reaction, optical isomer of (R) or (S) can be freely obtained by a suitable selection of the antipode of the asymmetric ligand.

The reduction enzyme may be used in the asymmetric reduction as well. In that case, (R) or (S) optical isomers may be freely manufactured by a suitable selection of the reduction enzyme.

Alternatively, racemic mixture can be made to react with an optically active resolving reagent (e.g. cis-benzamidocyclohexanecarbonyl chloride, trans-benzamidocyclohexanecarbonyl chloride, trans-cyclohexanedicarboxylic acid anhydride, etc.), the resulting diastereomer is separated by means of fractional crystallization or chromatography and then hydrolyzed to give the above optically active substances. When the resulting diastereomer is a carboxylic acid, the diastereomer may be further treated with a suitable base to afford diastereomer salt with good crystallinity.

Further, the above optical isomers may also be manufactured by subjecting a racemic mixture to a high performance liquid chromatography using an optically active column such as CHIRALCEL OD or CHIRALCEL OF.

The optical active substance wherein R² is carboxy may also be prepared by treating the racemic mixture with optically active base (e.g. brucine, quinine or α-methylbenzylamine) by utilizing its acidity and by separating the resulting diastereomer by means of fractional crystallization followed by treating with an acid.

The starting material (II) used in the present invention may, for example, be manufactured in accordance with the following route.

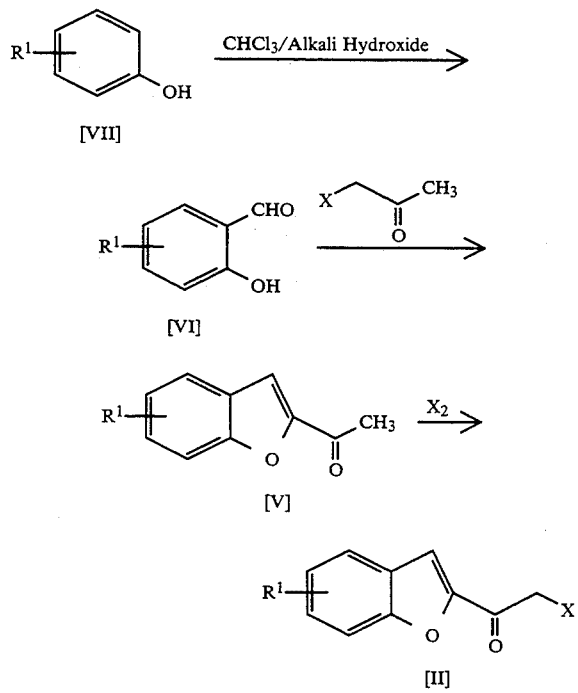

wherein the meanings of R¹ and X are the same as those defined already.

The starting material (VII) in the above route is known or can be manufactured in accordance with conventional means.

The compound (VII) is dissolved in alcoholic solvent such as methanol or ethanol and can be made to react with chloroform and aqueous solution of alkali hydroxide (e.g. sodium hydroxide or potassium hydroxide) at 50°–80° C. to give the compound (VI).

The reaction time may vary depending upon the type of the compound (VII) and reaction temerature but, usually, 30 minutes to 5 hours will be suitable. The preferred amount of the alkali hydroxide to one mol of the compound (VII) is 2 to 10 mol.

Then, the compound (VI) and haloacetone (e.g. chloroacetone, bromoacetone or iodoacetone) are made to react in accordance with the reaction of the compound (II) with the compound (III) as herein above whereupon the compound (V) can be prepared.

Then, the resulting compound (V) can be made to react with halogen (e.g. bromine, chlorine or iodine) in a suitable solvent (e.g. chloroform, carbon tetrachloride, diethyl ether or N,N-dimethylformamide) at the temperature of $-20°$ to $80°$ C. to give a compound (II) (X is halogen).

The reaction time may vary depending upon the type of the compound (V) used and also upon the reaction temperature but, usually, 30 minutes to 24 hours will be suitable. Preferred amount of the halogen to one mol of the compound (V) is 0.9 to 1.2 mol.

The compound (II) wherein X is alkylsulfonyloxy or arylsulonyloxy may be manufactured by conventional method starting from the compound (II) wherein X is halogen prepared as hereinabove.

Another starting material (III) is known or may be manufactured in accordance with known methods.

The compound of the present invention is effective for the therapy of the diseases wherein the concentration of Lp(a) in blood is high and also of the diseases caused thereby. Besides the above pharmacological action, the compound of the present invention exhibits a lowering action of lipid concentration in blood. Such a fact is a characteristic feature of the present invention.

Thus, the pharmaceutical composition of the present invention is effective as a prevention and a therapy of the arteriosclerosis caused by hyperlipemia and, further, is applicable to the therapy of the following symptoms.

They are cardiac infarction, coronary diseases including restenosis after PTCA treatment, angina pectoris and ischemic heart diseases caused by coronary diseases, cerebral infarction including cortical branch and perforator branch farctions and thrombosis as well as arteriosclerosis caused by that.

Compounds which lower the lipid concentration in blood have been known already but, so far as those having 2-(1-hydroxy-2-phenoxyethyl)benzofuran and 2-(phenoxyacetyl)benzofuran structures which are fundamental skeletons of the present invention have not been reported yet.

When the compounds of the present invention are given as drugs, they are given as they are or in a form of a pharmaceutical composition containing, for examle, 0.1–99.5% or, preferably, 0.5–90% of the compound in pharmaceutically-acceptable, nontoxic and inert carrier to animals including human being.

As to the carrier, one or more which is/are selected from solid, semisolid and liquid diluents, fillers and other auxiliary agents for pharmaceutical preparations. It is recommended that the pharmaceutical compositions are administered in a unit dosage form. The pharmaceutical compositions of the present invention may be administered via vein, mouth, tissue, local part (e.g. via skin) or rectum. Needless to say, the dosage form suitable for each administration route is chosen. Oral administration is particularly preferred.

The dose as a pharmaceutical composition for therapy of diseases of high Lp(a) concentration in blood is preferably set up by taking the state of the patients (e.g. age and body weight), administration route, type and degree of the diseases, etc. into consideration but, usually, the common dose of the effective amount of the present invention compound is 50–600 mg/day or, preferably, 100–300 mg/day per person.

In some cases, the dose may be less than the above or, in some other cases, more dose than the above range may be necessary. It is also possible to give twice or thrice daily by dividing the daily dose into two or three.

The same or similar dose may be applied for prevention and for therapy of arteriosclerosis and others.

Oral administration may be carried out by solid or liquid unit dosage form such as, for example, powder, diluted powder, tablets, sugar-coated agents, capsules, granules, suspensions, liquids, syrups, drops, sublingual agents, and the like.

Powder may be manufactured by making the active substance into suitable fine size. Diluted powder may be manufactured by making the active substance into suitable fine size followed by mixing with similarly fine pharmaceutical carrier such as, for example, starch, mannitol and other edible carbohydrates and others. If necessary, seasonings, preservatives, dispersing agents, colouring agents, perfumes, etc. may be mixed therewith.

Capsules may be manufactured by filling the above-mentioned powder or diluted powder or the granules (Which will be referred to in the item of tablets) into capsule sheaths made, for example, of gelatin. It is also possible that lubricants or fluidizing agents (e.g. colloidal silica, talc, magnesium stearate, calcium stearate and solid polyethylene glycol) is mixed with the powders followed by subjecting to the filling step. Addition of disintegrating agents or solubilizing agents such as, for example, carboxymethyl cellulose, carboxymethylcellulose calcium, lowly-substituted hydroxypropylcellulose, croscarmellose sodium, carboxymethyl starch sodium, calcium carbonate, sodium carbonate, etc. is effective in improving the effectiveness of the drug when the capsules are taken.

Further, the fine powder of the present invention compound is suspended/dispersed in vegetable oil, polyethylene glycol, glycerol or surface active agent followed by packing with gelatine sheet to give soft casules. Tablets may be prepared by preparing powder mixture by adding diluents, making into granules or slugs, adding disintegrating agents or lubricants thereto and making into tablets. The powder mixture may be prepared by mixing the suitably powdered substance with the above diluents and bases and, if necessary, mixed with binders (e,g. carboxymethylcellulose sodium, methylcellulose, hydroxypropylmethylcellulose, gelatin, polyvinylpyrrolidone, polyvinyl alcohol, etc.), dissolution-retarding agents (e.g. paraffin), reabsorbing agents (e.g. quaternay salts) and adsorbers (e.g. bentonite, kaolin, dicalcium phosphate, etc.). The powder mixture may be firstly wetted with a solution of binders (such as syrup, starch paste, gum arabic or cellulose) or aqueous solution of polymer, stirring/mixing and drying followed by pulverizing to give granules. Instead of making the powder into granules as such, the powder may be first tableted and the resulting slug of incomplete shape is pulverized to give granules.

The granules prepared as such may be mixed with lubricants (such as stearic acid, stearates, talc, mineral oil, etc.) so that adhesion to each other can be prevented. The lubricated mixture prepared as such is then tableted. The tablet prepared as such may be coated with film or with sugar.

Alternatively, the drug may be directly tableted after mixing with flowing and inert carrier without the step of prearing granules or slugs. Transparent or semitransparent protective coating comprising closed shellac coating, the coating of sugar or polymer material or a brushing coating comprising wax may be used as well.

Other types of preparations for oral use such as, for example, solution, syrup, elixir, etc. may be also made into unit dosage form wherein certain amount of a drug contains certain concentration of the drug. Syrup may be prepared by dissolving the compound into suitable aqueous solution with flavor. Elixir is manufactured using a alcoholic and nontoxic carrier. Suspension is manufactured by dispersing the compound into nontoxic carrier. If necessary, solubilizing agents or emulsifiers (e.g. ethoxylated isostearyl alcohols and polyoxyethylene sorbitol esters), preservatives, flavor-giving agents (e.g. peppermint oil and saccharine) may be added thereto.

If necessary, the unit dosage form for oral administration may be made into microcapsules. Said form may be coated or embedded in polymers or in wax so that the acting time can be elongated or sustained released action may be resulted.

Administration into tissue may be carried out by the liquid unit dosage form for hypodermic, intramuscular or intravenous injection (such as, for example, solution or suspension). They may be manufactured by suspending or dissolving certain amount of the compound into nontoxic liquidal carrier (such as aqueous or oily medium) meeting with the object of the injection followed by subjecting the suspsension or the solution to sterilization. In order to make the injection solution isotonic, nontoxic salt or salt solution may be added thereto. Further, stabilizers, preservatives, emulsifiers or the like may be simultaneously used as well.

Rectal administration can be carried out by the use of suppositories or the like which is prepared by dissolving or suspending the compound into low-melting and water-soluble or water-insoluble solid such as polyethylene glycol, cacao butter, semisynthetic fat/oil (e.g. Witepsol [trademark]), higher esters (e.g. myristyl palmitate) and a mixture thereof.

BEST MODE OF CARRYING OUT THE INVENTION

The present invention will be further illustrated by way of the referential examples, working examples, test examles and the manufacturing examples of the drugs of the present invention.

REFERENTIAL EXAMPLE

2-Bromoacetyl-5-tert-butylbenzofuran

Step 1: 5-tert-Butylsalicylaldehde 4-tert-Butylphenol (180.3 g) was dissolved in 95% ethanol, a solution of 345.6 g of sodium hdroxide in 800 ml of water was added and, with stirring, 229.2 g of chloroform was droped thereinto keeping the reaction temperature at 65°–75° C. After completion of the dropping, the reaction temperature was kept at 70°–75° C. and stirred for 1 hour. After cooling the reaction mixture, it was poured into diluted hydrochloric acid and the resulting oil was extracted with 1.5 liters of ether. The extract was washed with water twice, dried over anhydrous magnesium sulfate, concentrated in vacuo, the residue (220 g) was dissolved in 1.1 liters of isopropyl ether, the solution was extracted with 1.1 liters of 3% aqueous solution of sodium hydroxide and then extracted with 550 ml of 1% aqueous solution of sodium hydroxide. Aqueous layer was neutralized with concentrated hydrochloric acid, the resulting oil was extracted with ethyl acetate, the extract was washed with water twice, dried over anhydrous magnesium sulfate, concentrated in vacuo and the residue was distilled in vacuo to give 97.45 g of oil. B.p. 129°–135° C./5 mmHg.

Step 2: 2-Acetyl-5-tert-butylbenzofuran 5-tert-Butylsalicylaldehyde (163 g) was dissolved in 1.5 liters of acetonitrile, 252.5 g of anhydrous potassium carbonate was added and 84.6 g of chloroacetone was dropped into the mixture with stirring at room temperature. After completion of the dropping, the reaction mixture was stirred for 8 hours and then insoluble matters were filtered off. The filtrate was concentrated in vacuo and the residue was dissolved in ethyl acetate followed by washing with water twice. The ethyl acetate layer was dried over anhydrous magnesium sulfate and concentrated in vacuo. The residue was crystallized by adding isopropyl ether thereto followed by filtering to give 120.5 g of crystals. M.p. 99°–101° C.

Step 3: 2-Bromoacetyl-5-tert-butylbenzofuran

2-Acetyl-5-tert-butylbenzofuran (86.5 g) was dissolved in 800 ml of ether and, with stirring at room temperature, 63.9 g of bromine was dropped thereinto. When the crystals started to be separated, the reaction mixture was cooled with ice water. After completion of the dropping, the mixture was stirred for 30 minutes, the reaction mixture was poured into ice water and, until the crystals were dissolved, ethyl acetate was added thereto. The organic layer was washed with water for three times, dried over anhydrous magnesium sulfate, concentrated in vacuo and n-hexane was added to the residue to crystallize followed by filtrating to give 100.1 g of crystals. M.p. 100°–102° C.

In accordance with the same manner as the Referential Example, the following compounds were manufactured:

2-Bromoacetyl-5-chlorobenzofuran
2-Bromoacetyl-5-isopropylbenzofuran and
2-Bromoacetylbenzofuran

EXAMPLE 1

5-tert-Butyl-2-(4-methoxycarbonylphenoxyacetyl)benzofuran and
5-tert-butyl-2-[1-hydroxy-2-(4-methoxycarbonylphenoxy)ethyl]benzofuran 1) 5-tert-Butyl-2-(4-methoxycarbonylphenoxyacetyl)-benzofuran Methyl p-hydroxybenzoate (72.1 g) was dissolved in 800 ml of acetonitrile, 65.54 g of anhydrous potassium carbonate was added and, with stirring at room temperature, a solution of 140 g of 2-bromoacetyl-5-tert-butylbenzofuran in 1,000 ml of acetonitrile was dropped thereinto within 2 hours. After completion of the dropping, the mixture was stirred for 2 hours, the reaction mixture was poured into aqueous hydrochloric acid and the resulting crystals were collected by filtration followed by washing with water. The crystals were then dissolved in ethyl acetate, washed with water twice, the ethyl acetate layer was dried over anhydrous magnesium sulfate, concentrated in vacuo and ether was added to the residue followed by filtration to give 124 g of crystals. M.p. 148°–150° C.

IR (KBr) cm$^{-1}$: 2940, 1700, 1600, 1545, 1510

2) 5-tert-Butyl-2-[1-hydroxy-2-(4-methoxycarbonylphenoxy)ethyl]benzofuran 5-tert-Butyl-2-(4-methoxycarbonylphenoxyacetyl)-benzofuran (124 g) was suspended in 980 ml of methanol and, with cooling with ice and stirring, 30 g of sodium borohydride was added thereto little by little. After stirring for 2 hours, 8.8 g of sodium borohydride was added and the mixture was stirred at room temperature for 4 hours. The reaction mixture was poured into 10 liters of ice water (acidified with hydrochloric acid) and the resulting crystals were collected by filtration. The crystals were dissolved in chloroform, the solution was washed with water twice and the chloroform layer was dried over anhydrous magnesium sulfate followed by concentrating in vacuo to give 120.1 g of crystals. M.p. 110°–112° C.

Elementary Analysis for $C_{22}H_{24}O_5$ Calcd (%) C:71.72, H:6.57 Found (%) C:71.59, H:6.43

By the same manner as in Example 1, the following compounds were manufactured.

EXAMPLE 2

5-Chloro-2-(4-methoxycarbonylphenoxyacetyl)benzofuran and
5-chloro-2-[1-hydroxy-2-(4-methoxycarbonylphenoxy)ethyl]benzofuran 1) 5-Chloro-2-(4-methoxycarbonylphenoxyacetyl)benzofuran M.p. 145°–147° C. IR (KBr) cm$^{-1}$: 1710, 1695, 1600, 1560.

2) 5-Chloro-2-[1-hydroxy-2-(4-methoxycarbonylphenoxy)ethyl]benzofuran

M.p. 100°–103° C. Elementary Analysis for $C_{18}H_{15}ClO_5$ Calcd (%) C:62.35, H:4.36 Found (%) C:62.22, H:4.57

EXAMPLE 3

5-Isopropyl-2-(4-methoxycarbonylphenoxyacetyl)benzofuran and
2-[1-hydroxy-2-(4-methoxycarbonylphenoxy)ethyl]-5-isopropylbenzofuran 1) 5-Isopropyl-2-(4-methoxycarbonylphenoxyacetyl)benzofuran M.p. 95°–97° C. IR (KBr) cm$^{-1}$: 2950, 1705, 1695, 1600, 1510.

2) 2-[1-Hydroxy-2-(4-methoxycarbonylphenoxy)ethyl]-5-isopropylbenzofuran

M.p. 70°–72° C. Elementary Analysis for $C_{21}H_{22}O_5$ Calcd (%) C:71.17, H:6.26 Found (%) C:71.32, H:6.15

EXAMPLE 4

5-tert-Butyl-2-[2-(4-carboxyphenoxy)-1-hydroxyethyl]benzofuran 5-tert-Butyl-2-[1-hydroxy-2-(4-methoxycarbonylphenoxy)ethyl]benzofuran (112 g) obtained in Example 1 was dissolved in 1.5 liters of methanol, a solution of 24.3 g of sodium hydroxide dissolved in 400 ml of water was added thereto and the mixture was heated to reflux for 2 hours. The reaction mixture was concentrated in vacuo, ice water was added to the residue and the mixture was acidified with concentrated hydrochloric acid to give crystals. The crystals collected by filtration were dissolved in ethyl acetate, the solution was washed with water and dried over anhydrous magnesium sulfate followed by concentrating in vacuo whereupon the residue is crystallized. This was dried and recrystallized from acetonitrile to give 88.3 g of crystals. M.p. 175°–177° C.

Elementary Analysis for $C_{21}H_{22}O_5$ Calcd (%) C:71.17, H:6.26 Found (%) C:71.03, H:6.46

EXAMPLE 5

2-[2-(4-Carboxyphenoxy)-1-hydroxyethyl]-5-chlorobenzofuran

The same operation as in Example 4 was conducted using 5-chloro-2-[1-hydroxy-2-(4-methoxycarbonylphenoxy)ethyl]benzofuran obtained in Example 2 to give crystals. M.p. 157°–159° C.

Elementary Analysis for $C_{17}H_{13}ClO_5$ Calcd (%) C:61.36, H:3.94 Found (%) C:60.85, H:4.10

EXAMPLE 6

2-[2-(4-Carboxyphenoxy)-1-hydroxyethyl]5-isopropylbenzofuran

2-[1-Hydroxy-2-(4-methoxycarbonylphenoxy)ethyl]-5-isopropylbenzofuran obtained in Example 3 was treated by the same method as in Example 4 to give crystals. M.p. 148°–150° C.

Elementary Analysis for $C_{20}H_{20}O_5$ Calcd (%) C:70.58, H:5.92 Found (%) C:70.39, H:5.76

EXAMPLE 7

2-[2-(4-Carboxyphenoxy)-1-hydroxyethyl]benzofuran

2-[1-Hydroxy-2-(4-methoxycarbonylphenoxy)ethyl]benzofuran prepared by the same method as in Example 1 was treated by the same method as in Examle 4 to give crystals. M.p. 153°–155° C.

Elementary Analysis for $C_{17}H_{14}O_5$ Calcd (%) C:68.45, H:4.73 Found (%) C:68.67, H:4.59

EXAMPLE 8

2-[2-(4-Carboxyphenoxy)-1-hydroxyethyl]-5-isopropylbenzofuran sodium salt

Metal sodium (2.3 g) was dissolved in 200 ml of ethanol and 35.7 g of 2-[2-(4-carboxyphenoxy)-1-hydroxyethyl]-5-isopropylbenzofuran obtained in Example 6 was dissolved thereinto. The reactin mixture was concentrated in vacuo and acetone was added to the residue whereupon crystals were obtained. The crystals collected therefrom by filtration were recrystallized from ethanol to give 26.5 g of crystals. M.p. 305° C. (decomposition)

Elementary Analysis for $C_{20}H_{19}NaO_5.\frac{1}{2}H_2O$ Calcd (%) C:64.69, H:5.43 Found (%) C:64.82, H:5.27

EXAMPLE 9

2-[2-(4-Carboxyphenoxy)-1-hydroxyethyl]-5-isopropylbenzofuran calcium salt

2-[2-(4-Carboxyphenoxy)-1-hydroxyethyl]-5-isopropylbenzofuran sodium salt (37.1 g) was dissolved in 300 ml of water. A solution of 5.55 g of calcium chloride dissolved in 50 ml of water was added to the above-obtained solution. The crystals separated out therefrom were collected by filtration and washed with water and then with acetone to give 34.6 g of crystals. M.p. not lower than 300° C.

Elementary Analysis for $C_{40}H_{38}CaO_{10} \cdot 2H_2O$ Calcd (%) C:63.65, H:5.61 Found (%) C:63.48, H:5.77 IR (KBr) cm$^{-1}$: 3340, 2950, 1600, 1540

EXAMPLE 10

2-[1-Hydroxy-2-(4-hydroxymethylphenoxy)ethyl]-5-isopropylbenzofuran

Step 1: 5-Isopropyl-2-(4-formylphenoxyacetyl)benzofuran p-Hydroxybenzaldehyde (12.2 g) was dissolved in 200 ml of N,N-dimethylformamide, 13.8 g of anhydrous potassium carbonate was added and, with stirring at room temperature, 28.1 g of 2-bromoacetyl-5-isopropylbenzofuran was added thereto within 30 minutes. The mixture was stirred at room temperature for 2 hours more. The reaction mixture was poured into aqueous solution of hydrochloric acid and the resulting crystals were collected by filtration and washed with water. The crystals were then dissolved in ethyl acetate, the solution was washed with water and the ethyl acetate layer was dried over anhydrous magnesium sulfate and concentrated in vacuo whereupon the residue was crystallized. Ether was added to the crystals and then collected by filtraton to give 18.1 g of crystals.

Step 2: 2-[1-Hydroxy-2-(4-hydroxymethylphenoxy)ethyl]-5-isopropylbenzofuran

5-Isopropyl-2-(4-formylphenoxyacetyl)benzofuran (18.1 g) was dissolved in 200 ml of methanol. Sodium borohydride (2 g) was added thereto with stirring and cooling with ice and the mixture was stirred for 1 hour. The reaction mixture was poured into aqueous solution of hydrochloric acid and the crystals separated out therefrom were collected by filtration followed by recrystallization from ethyl acetate/n-hexane to give 16.5 g of crystals. M.p. 98°–100° C.

Elementary Analysis for $C_{20}H_{22}O_4$ Calcd (%) C:73.60, H:6.79 Found (%) C:73.45, H:6.68

EXAMPLE 11

(+)-5-tert-Butyl-2-[2-(4-carboxyphenoxy)-1-hydroxyethyl]benzofuran 5-tert-Butyl-2-[1-hydroxy-2-(4-methoxycarbonylphenoxy)ethyl]benzofuran (4.16 g) obtained in Example 1 was suspended in 30 ml of toluene, 1.7 g of triethylamine was added, then 3.0 g of (+)-cis-2-benzamidocyclohexanecarbonyl chloride was dropped thereinto at room temperature with stirring and the mixture was stirred for 18 hours. The mixture was further stirred at 80° for 1.5 hours, the reaction mixture was poured into ice water, the mixture was extracted with ethyl acetate, the extract was washed with aqueous solution of sodium hydroxide followed by washing with water, dried over anhydrous magnesium sulfate and concentrated to give dark brown oil. Methanol (25 ml) was added to the oil, the mixture was heated to dissolve and cooled to give 1.26 g of crystals. Recrystallization from methanol gave 760 mg of white crystals. M.p. 147°–148° C.

The resulting crystals were heated to reflux for 1.5 hours in a mixture of 40 ml of methanol and 11 ml of 2% aqueous solution of sodium hydroxide, the reaction mixture was concentrated, the residue was dissolved in water, the solution was neutralized with hydrochloric acid, extracted with ethyl acetate, the extract was washed with 5% aqueous solution of potassium acetate and then with water, dried over anhydrous magnesium sulfate, concentrated and the residue was recrystallized from acetonitrile to give 282 mg of white crystals. M.p. 133°–135° C.

Elementary analysis for $C_{21}H_{22}O_5$ Calcd (%) C:71.17, H:6.26 Found (%) C:70.97, H:6.45 $[\alpha]_D = +1.98°$ (MeOH, c=1.00).

EXAMPLE 12

(−)-5-tert-Butyl-2-[2-(4-carboxyphenoxy)-1-hydroxyethyl]benzofuran

The same operations as in Example 11 were conducted using (−)-cis-2-benzamidocyclohexanecarbonyl chloride as the resolving reagent to give crystals. M.p. 134°–136° C.

Elementary analysis for $C_{21}H_{22}O_5$ Calcd (%) C:71.17, H:6.26 Found (%) C:71.07, H:6.38 $[\alpha]_D = -1.90°$ (MeOH, c=1.00).

EXAMPLE 13

2-(4-Benzyloxycarbonylphenoxyacetyl)-5-tert-butylbenzofuran

The same operations as in Example 1 were conducted to give crystals. M.p. 153°–155° C.

IR (KBr) cm$^{-1}$: 2940, 1695, 1600, 1505.

EXAMPLE 14

5-tert-Butyl-2-(4-carboxyphenoxyacetyl)benzofuran 2-(4-Benzyloxycarbonylphenoxyacetyl)-5-tert-butylbenzofuran (1 g) obtained in Example 13 was suspended in 15 ml of acetic acid and 2 ml of 47% hydrobromic acid and the mixture was stirred at 60° C. for 15 hours. The reaction mixture was cooled, poured into ice water, the mixture was extracted with ethyl acetate, the extract was washed with water, dried over anhydrous magnesium sulfate, concentrated in vacuo, ether was added to the residue and the mixture was filtered followed by recrystallization from acetonitrile to give 510 mg of crystals. M.p. 209.5°–211° C.

Elementary analysis for $C_{21}H_{20}O_5$ Calcd (%) C:71.58, H:5.72 Found (%) C:71.38, H:5.65

EXAMPLE 15

5-tert-Butyl-2-[2-(4-carboxyphenoxy)-1-hydroxyethyl]benzofuran sodium salt

The same operations as in Example 8 were conducted using 5-tert-butyl-2-[2-(4-carboxyphenoxy)-1-hydroxyethyl]benzofuran obtained in Example 4 to give crystals. M.p. not lower than 300° C.

Elementary analysis for $C_{21}H_{21}NaO_5.\frac{1}{4}H_2O$ Calcd (%) C:66.22, H:5.69 Found (%) C:66.22, H:5.66 IR (KBr) cm$^{-1}$: 2950, 1600, 1590, 1540.

EXAMPLE 16

2-[1-Acetoxy-2-(4-acetoxymethylphenoxy)ethyl]-5-isopropylbenzofuran

2-[1-Hydroxy-2-(4-hydroxymethylphenoxy)ethyl]-5-isopropylbenzofuran (10 g) obtained in Example 10 was dissolved in 100 ml of pyridine, 20 ml of acetic anhydride was added, the mixture was stirred at room temperature for 24 hours, the reaction mixture was poured into ice water and the crystals separated out therefrom were filtered, dried and recrystallized from methanol to give 7.3 g of crystals. M.p. 74°–76° C.

Elementary analysis for $C_{24}H_{26}O_6$ Calcd (%) C:70.23, H:6.38 Found (%) C:70.46, H:6.14

EXAMPLE 17

2-[1-Acetoxy-2-(4-carboxyphenoxy)ethyl]-5-isopropylbenzofuran

2-[1-Hydroxy-2-(4-hydroxymethylphenoxy)ethyl]-5-isopropylbenzofuran (10 g) obtained in Example 6 was dissolved in 100 ml of pyridine, the mixture was stirred at room temperature for 24 hours with 10 ml of acetic anhydride, poured into ice water, the mixture was acidified with concentrated hydrochloric acid and the crystals separated out therefrom were filtered, dried and recrystallized from ethyl acetate/n-hexane to give 8.2 g of crystals. M.p. 135°–137° C.

Elementary analysis for $C_{22}H_{22}O_6$ Calcd (%) C:69.09, H:5.79 Found (%) C:68.86, H:5.93

EXAMPLE 18

5-tert-Butyl-2-[2-(4-carboxyphenoxy)ethyl]benzofuran

Diethylene glycol (10 ml) and 285 mg of hydrazine monohydrate were added to 5-tert-butyl-2-(4-carboxyphenoxyacetyl)benzofuran (1 g) obtained in Example 14 and the mixture was stirred at 90° C. for 40 minutes. Potassium hydroxide (398 mg) was added to the mixture and then heated at 120° C. for 2 hours with stirring and further heated at 180°–190° C. for 3 hours. The reaction mixture was poured into aqueous solution of hydrochloric acid and the crystals separated out therefrom were filtered to give 0.86 g of crystals.

Elementary analysis for $C_{21}H_{22}O_4$ Calcd (%) C:74.53, H:6.55 Found (%) C:74.36, H:6.68

Test Example

As hereunder, the result of pharmacological tests for showing the usefulness of the representative compounds of the present invention will be given.

1) An action of lowering total cholesterol (TC) in serum using normal rhesus monkeys.

Test Method: Male rhesus monkeys of 2–5 years age (body weight: 3.0–6.4 kg; Experiment No.1) or male rhesus monkeys of 2–6 years age (body weight: 3.5–8.0 kg; Expt. Nos. 2, 3 and 4) were subjected to the experiments. During the experiment, solid feed (manufactured by Oriental Yeast) was given at the dose of 150 g once daily. Each group consisted of 2 to 6 monkeys. The substance to be tested was in a form of suspension in 0.5% methylcellulos solution. The suspension was given orally using rubber probe at the dose of 30, 50 or 100 mg/kg for seven days (Expt. Nos. 1 and 2(2)) or for 28 days (Expt. Nos. 2(1), 3 and 4). Blood was taken from saphena in lower limbs one week and immediately before the administration and also 7, 14, 21 and 28 days after the administration of the suspension whereby serum TC was measured. The change rate of serum TC was calculated by the following expression.

The change rate of serum $TC=(ATC-BTC)/BTC\times 100$

In the expression, ATC is the TC after administration of the substance tested while BTC is the TC before the administration (average of those one week and immediately before the administration). The result is given in Table 1 wherefrom it is clear that the compounds of the present invention exhibit a lowering action for serum TC.

TABLE 1

| Experiment Number | Substance Used (Example No.) | Dose (mg/kg) | Numbers of Animals | TC Change Rate (%) after | | | |
|---|---|---|---|---|---|---|---|
| | | | | 7 | 14 | 21 | 28 days |
| 1(1) | (Control) | — | 2 | 7 | | | |
| 1(2) | Example 6 | 100 | 2 | −42 | | | |
| 2(1) | (Control) | — | 4 | −1 | 3 | 7 | 4 |
| 2(2) | Example 10 | 100 | 2 | −32* | | | |
| 3(1) | (Control) | — | 4 | −8 | −5 | −8 | −11 |
| 3(2) | Example 8 | 50 | 3 | −31** | −31 | −44* | −51* |
| 4(1) | (Control) | — | 6 | 10 | 1 | 1 | 1 |
| 4(2) | Example 9 | 30 | 3 | −19** | −34** | −29** | −24** |
| 4(3) | Bezafibrate | 100 | 3 | −13* | −10 | 3 | −7 |

* and ** mean that significant differences were noted at the risk of 5% and 1%, respectively.

2) Serum TC lowering action in normal crab-eating macaques.

Test Method: Male crab-eating macaques (body weight: 2.5–6.6 kg) were subjected to the experiments. During the expriment period, the feed (manufactured by Oriental Yeast) containing 0.1% (Expt. No. 1) or 0.3% (Expt. No. 2) of the compound of Example 4 was given once daily a 35 g/kg for 5 weeks (0.1%) or for 8 weeks (0.3%). Usual feed for monkeys was given to the control group. Blood was taken immediately before the administration and 1, 2 and 5 weeks after the administration in the case of 0.1% mixed feed or, in the case of 0.3% mixed feed, immediately before and 2, 4, 6 and 8 weeks after the administration. All operations for taking blood were conducted prior to giving the feed and the serum TC therein was measured. The change rate of the serum TC was calculated by the following expression.

The change rate of serum $TC=(ATC-BTC)/BTC\times 100$

In the expression, ATC is the TC after administration of the substance tested and BTC is the TC immediately before administration. The result is given in Tables 2 and 3 wherefrom it is clear that the compound of the present invention exhibits a serum TC lowering action.

TABLE 2

| Experiment Number | Substance Used (Example No.) | Concn. of the Substance in the Feed | Numbers of Animals | TC Change Rate (%) after | | |
|---|---|---|---|---|---|---|
| | | | | 1 | 2 | 5 weeks |
| 1 (1) | (Control) | — | 5 | 6 | 14 | 2 |
| 1 (2) | Example 4 | 0.1% | 7 | 16 | −18** | −31** |

** means that significant difference was noted at the risk of 1%.

TABLE 3

| Experiment Number | Substance Used (Example No.) | Concn. of the Substance in the Feed | Numbers of Animals | TC Change Rate (%) after | | | |
|---|---|---|---|---|---|---|---|
| | | | | 2 | 4 | 6 | 8 weeks |
| 2(1) | (Control) | — | 6 | 1 | −5 | −7 | −3 |
| 2(2) | Example 4 | 0.3% | 3 | −32* | −46** | −42* | −37* |

* and ** mean that significant differences were noted at the risk of 5% and 1%, respectively.

3) Acute Toxicity

Mice of ddY-strain (7 weeks age; four mice per group) were fasted overnight, the compound of Example 4 of the present invention suspended in 0.5% methylcellulose solution was orally administered at 2 g/kg and the general symptoms until 3 hours after that and those until one week thereafter were checked.

The result was that no animals tested were dead and that no abnormal symptoms were noticed.

4) Influence of the compound of the present invention on Lp(a)

Five to six crab-eating monkeys (male; body weight ranging 5-9 kg) as one group were fed and, to the group administered with the test sample, the feed containing 0.3% of this invention compound (that of Example 4) was fed while, to the control group, usual feed was given. The Lp(a) concentrations in the plasma were measured by the following method at the initiation of the administration, 13 weeks thereafter and 5 weeks after completion of the administration. The result is given in Table 4.

TABLE 4

An Action of the Compound of this Invention (Example 4) for Lowering Lp(a) in Plasma in Crab-Eating Monkeys

| Group | Numbers of the Animals | Plasma Lp(a) (mg/dl) | | |
|---|---|---|---|---|
| | | Immed. after administration | 13 Weeks thereafter | 5 Weeks after Completion of administration |
| Control | 6 | 71.5 ± 11.1 | 59.1 ± 19.3 | 71.3 ± 12.8 |
| Administered Group | 5 | 73.2 ± 8.5 | 9.2 ± 1.2* | 60.1 ± 7.9 |

*: $p < 0.05$ (tested to the control by means of Student's t-test)
Values are given as average ± S.E.

It is clear that the compound of the present invention significantly loweres the plasma Lp(a) of crab-eating monkeys. [Method of measuring the Lp(a) values]

Commercially-available kit manufactured by Biopool Co, was used. In accordance with the procedures as given in the kit, PET buffer and sample buffer were prepared. To 20 μl of the plasma was added 1 ml of sample buffer and to 10 μl or 20 μl the resulting diluted liquid was further added 1.01 ml or 1 ml of the sample buffer to that the liquid diluted to an extent of 5202 times or 2601 times was prepared. In accordance with the steps as instructed by the kit, each 20 μl of the diluted sample was added to each well and measurement was conducted by duplicate. The result was calculated from the working curve prepared from the data obtained for the standard human Lp(a) in the kit.

5) Action of the compounds of the present invention to lipid biosynthesis by tissue slices of liver of rat Test method: Krebs-Ringer-Bicarbonate solution (1 ml) containing 1 mM of $^{14}$C-acetic acid and 10 μg/ml of the test substance was added to 100 mg of liver slices of rat, the air was substituted with a mixed gas (oxygen:carbon dioxide=95:5) and incubation was conducted at 37° C. for 2 hours. After completion of the reaction, 15% ethanolic solution of potassium hydroxide was added and saponification was conducted at 75° C. for 2 hours. A part of the saponified solution was subjected to a measurment of protein. Residual saponified solution was extracted with petroleum ether and the radioactivity of the petroleum ether layer was measured to determine the cholesterol synthesizing activity. The aqueous layer was acidified with 6N hydrochloric acid, extracted with petroleum ether and the radioactivity of the extract was measured to determine fatty acid synthesizing activity. The values were expressed in terms of percentage to the control after calculating the mol numbers (nmol/mg) of the $^{14}$C-acetic acid incorporated into each extract per protein (nmol/mg protein).

The result is given in Table 5 wherefrom the inhibitory action for fatty acid synthesis and for cholesterol synthesis of the compounds of the present invention is clear.

TABLE 5

| Compound Given (Ex. No.) | Amount Added (μg/ml) | Fatty Acid Synth. (%) | | Cholesterol Synth. (%) | |
|---|---|---|---|---|---|
| | | Expt. 1 | Expt. 2 | Expt. 1 | Expt. 2 |
| Control | — | 100 | 100 | 100 | 100 |
| Example 4 | 10 | 20 | 12 | 41 | 27 |
| Example 11 | 10 | 12 | 18 | 35 | 24 |
| Example 12 | 10 | 16 | 14 | 33 | 27 |

6) Action of the compounds of the present invention to lipid biosynthesis of tissue slices of liver of rat (part 2)

The activity of the present invention compound was measured by the same manner as above 5). The values were expressed in terms of percentage to the control after calculating the mol numbers (nmol/mg) of the $^{14}$C-acetic acid incorporated into each extract per protein (nmol/mg protein). The result is given in Table 6 wherefrom it is clear that the compounds of the present invention exhibit inhibitory action or fatty acid synthesis and for cholesterol synthesis.

TABLE 6

| Compound Given (Ex. No.) | Amount Added (μg/ml) | Fatty Acid Synthesis (%) | Cholesterol Synthesis (%) |
|---|---|---|---|
| Control | — | 100 | 100 |
| Example 4 | 10 | 29 | 61 |
| Example 14 | 10 | 32 | 64 |
| Example 17 | 10 | 33 | 66 |

Manufacturing Example 1

Tablets for Oral Use

Prescription: Each tablet (180 mg) contains

| | |
|---|---|
| The compound of Examle 4 | 100 mg |
| Lactose | 45 mg |
| Corn starch | 20 mg |
| Hydroxypropylcellulose of low degree of substitution | 9 mg |

| -continued | |
|---|---|
| Partially-hydrolyzed polyvinyl alcohol | 5 mg |
| Magnesium stearate | 1 mg |

The above ingredients except polyvinyl alcohol and magnesium stearate were homogeneously mixed and subjected to a wet tabletting method using aqueous solution of polyvinyl alcohol as a binder to give granules. They were mixed with magnesium stearate and the mixture was made into tablets using a tabletting machine for oral use in a form of 8 mm diameter and mg weight per tablet.

Manufacturing Example 2

Hard Capsules

Prescrition: Each capsule (285 mg) contains

| The compound of Example 4 | 100 mg |
|---|---|
| Lactose | 107 mg |
| Microcrystalline cellulose | 10 mg |
| Magnesium stearate | 3 mg |

The above ingredients were homogeneously mixed and each 220 mg of the mixture was filled in a capsule (#2 size) using a capsule filling machine whereupon hard capsules (each capsule weighed 285 mg) were prepared.

Manufacturing Example 3

Granules

Prescription: Each one gram of the granules contains

| The compound of Example 4 | 100 mg |
|---|---|
| Lactose | 790 mg |
| Hydroxypropylcellulose of low degree of substitution | 70 mg |
| Hydroxypropylcellulose | 40 mg |

The above ingredients were homogeneously mixed, kneaded and granulated using a granulatiung machine to give granules (each granule was with 0.7 mm diameter).

We claim:

1. A compound of formula (I) or pharmacologically-acceptable salt thereof.

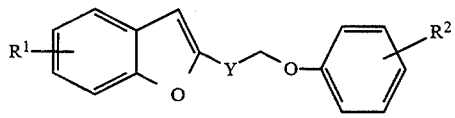

wherein $R^1$ is hydrogen, halogen or alkyl; $R^2$ is alkoxycarbonyl, aralkyloxycarbonyl, carboxy, hydroxyalkyl or acyloxyalkyl; Y is >CHOH, >CHOZ, >CH$_2$ or >CO; and Z is acyl.

2. The compound according to claim 1, wherein $R^1$ is hydrogen halogen or alkyl of 1 to 7 carbon atoms, $R^2$ is alkyoxycarbonyl having 1 to 7 carbon atoms in the alkoxy moiety thereof, aralkyloxycarbonyl having 8 to 14 carbon atoms, carboxy, hydroxyalkyl having 1 to 7 carbon atoms or acyloxyalkyl having 1 to 11 carbon atoms in the acyl moiety and 1 to 7 carbon atoms in the alkyl moiety thereof; Y is >CHOH, >CHOZ, >CH$_2$ or >CO; and Z is acyl having 1 to 11 carbon atoms.

3. The compound according to claim 1, which is 5-tert-butyl-2-[2-(4-carboxyphenoxy)-1-hydroxyethyl]-benzofuran.

4. The compound according to claim 1, which is 2-[2-(4-carboxyphenoxy)-1-hydroxyethyl]-5-isopropylbenzofuran.

5. The compound according to claim 1, which is 2-[1-hydroxy-2-(4-hydroxymethylphenoxy)-ethyl]-5-isopropylbenzofuran.

6. The compound according to claim 1, which is (+)-5-tert-butyl-2-[2-(4-carboxyphenoxy)-1-hydroxyethyl]-benzofuran.

7. The compound according to claim 1, which is (−)-5-tert-butyl-2-[2-(4-carboxyphenoxy)-1-hydroxyethyl]benzofuran.

8. The compound according to claim 1, which is 5-tert-butyl-2-(4-carboxyphenoxyacetyl)-benzofuran.

9. The compound according to claim 1, which is 2-[1-acetoxy-2-(4-carboxyphenoxy)-ethyl]-5-isopropylbenzofuran.

10. A method of lowering blood serum Lp(a) in a human or a non-human animal, which comprises administering to the human or the non-human animal in need thereof an serum Lp(a) lowering effective amount of a compound according to claim 1.

11. A method of claim 10, wherein the lowering of serum Lp(a) is in a human or non-human animal, in need thereof, having arteriosclerosis, ischemic heart disease, cerebral infraction or restenosis after a percutaneous transluminal coronary angioplasty procedure.

12. A method of lowering blood serum cholesterol in a human or a non-human animal, which comprises administering to the human or non-human animal in need thereof, a blood serum cholesterol-lowering affective amount of a compound according to claim 1.

13. The method according to claim 10, wherein the compound is 5-tert-butyl-2-[2-(4-carboxyphenoxy)-1-hydroxyethyl]-benzofuran.

14. The method according to claim 10, wherein the compound is 2-[2-(4-carboxyphenoxy)-1-hydroxyethyl]-5-isopropyl-benzofuran.

15. The method according to claim 10, wherein the compound is 2-[1-hydroxy-2-(4-hydroxymethylphenoxy)-ethyl]-5-isopropylbenzofuran.

16. The method according to claim 10, which is (+)-5-tert-butyl-2-[2-(4-carboxyphenoxy)-1-hydroxyethyl]-benzofuran.

17. The method according to claim 10, which is (−)-5-tert-butyl-2-[2-(4-carboxyphenoxy)-1-hydroxyethyl]-benzofuran.

18. The method according to claim 10, which is 5-tert-butyl-2-(4-carboxyphenoxyacetyl)-benzofuran.

19. The method according to claim 10, which is 2-[1-acetoxy-2-(4-carboxyphenoxy)-ethyl]-5-isopropylbenzofuran.

20. The method according to claim 11, which is 5-tert-butyl-2-[2-(4-carboxyphenoxy)-1-hydroxyethyl]-benzofuran.

21. The method according to claim 11, which is 2-[2-(4-carboxyphenoxy)-1-hydroxyethyl]-5-isopropyl-benzofuran.

22. The method according to claim 11, which is 2-[1-hydroxy-2-(4-hydroxymethylphenoxy)-ethyl]-5-isopropylbenzofuran.

23. The method according to claim 11, which is (+)-5-tert-butyl-2-[2-(4-carboxyphenoxy)-1-hydroxyethyl]-benzofuran.

24. The method according to claim 11, which is (−)-5-tert-butyl-2-[2-(4-carboxyphenoxy)-1-hydroxyethyl]-benzofuran.

25. The method according to claim 11, which is 5-tert-butyl-2-(4-carboxyphenoxyacetyl)-benzofuran.

26. The method according to claim 11, which is 2-[1-acetoxy-2-(4-carboxyphenoxy)-ethyl]-5-isopropylbenzofuran.

27. The method according to claim 12, which is 5-tert-butyl-2-[2-(4-carboxyphenoxy)-1-hydroxyethyl]-benzofuran.

28. The method according to claim 12, which is 2-[2-(4-carboxyphenoxy)-1-hydroxyethyl]-5-isopropylbenzofuran.

29. The method according to claim 12, which is 2-[1-hydroxy-2-(4hydroxymethylphenoxy)-ethyl]-5-isopropylbenzofuran.

30. The method according to claim 12, which is (+)-5-tert-butyl-2-[2-(4-carboxyphenoxy)-1-hydroxyethyl]-benzofuran.

31. The method according to claim 12, which is (−)-5-tert-butyl-2-[2-(4-carboxyphenoxy)-1-hydroxyethyl]-benzofuran.

32. The method according to claim 12, which is 5-tert-butyl-2-(4-carboxyphenoxyacetyl)-benzofuran.

33. The method according to claim 12, which is 2-[1-acetoxy-2-(4-carboxyphenoxy)-ethyl]-5-isopropylbenzofuran.

34. A pharmaceutical composition for lowering the blood serum Lp(a), for lowering blood serum cholesterol, and/or for the prevention or treatment of arteriosclerosis, ischemic heart disease, cerebral infarction and/or restenosis after a percutaneous translumial coronary angioplasty procedure in an animal, including a human, which comprises a therapeutically effective amount of a compound according to claim 1 in combination with a pharmaceutically acceptable inert diluent or carrier therefor.

35. The composition according to claim 34, wherein the compound is 5-tert-butyl-2-[2-(4-carboxyphenoxy)-1-hydroxyethyl]-benzofuran.

36. The composition according to claim 34, which is 2-[2-(4-carboxyphenoxy)-1-hydroxyethyl]-5-isopropylbenzofuran.

37. The composition according to claim 34, which is 2-[1-hydroxy-2-(4-hydroxymethylphenoxy)-ethyl]-5-isopropylbenzofuran.

38. The composition according to claim 34, which is (+)-5-tert-butyl-2-[2-(4-carboxyphenoxy)-1-hydroxyethyl]-benzofuran.

39. The composition according to claim 34, which is (−)-5-tert-butyl-2-[2-(4-carboxyphenoxy)-1-hydroxyethyl]-benzofuran.

40. The composition according to claim 34, which is 5-tert-butyl-2-(4-carboxyphenoxyacetyl)-benzofuran.

41. The composition according to claim 34, which is 2-[1-acetoxy-2-(4-carboxyphenoxy)-ethyl]-5-isopropylbenzofuran.

42. The compound which is 2-bromoacetyl-5-tert-butylbenzofuran or 2-bromoacetyl-5-isopropylbenzofuran.

* * * * *